(12) United States Patent
Burrow

(10) Patent No.: US 9,480,782 B2
(45) Date of Patent: Nov. 1, 2016

(54) SURGICAL ASPIRATION AND IRRIGATION

(71) Applicant: R. Ashley Burrow, Suwanee, GA (US)

(72) Inventor: R. Ashley Burrow, Suwanee, GA (US)

(*) Notice: Subject to any disclaimer, the term of this patent is extended or adjusted under 35 U.S.C. 154(b) by 354 days.

(21) Appl. No.: 14/150,921

(22) Filed: Jan. 9, 2014

(65) Prior Publication Data

US 2014/0221909 A1 Aug. 7, 2014

Related U.S. Application Data

(60) Provisional application No. 61/752,225, filed on Jan. 14, 2013.

(51) Int. Cl.
*A61M 1/00* (2006.01)
*A61M 39/22* (2006.01)

(52) U.S. Cl.
CPC .......... *A61M 1/0062* (2013.01); *A61M 1/0064* (2013.01); *A61M 39/22* (2013.01)

(58) Field of Classification Search
CPC ........... A61M 5/3272; A61M 5/3271; A61M 2005/3228; A61M 25/0631; A61M 1/0058; A61M 1/0064; A61M 39/223; A61M 1/008; A61M 2210/0612
See application file for complete search history.

(56) References Cited

U.S. PATENT DOCUMENTS

| | | | | |
|---|---|---|---|---|
| 1,658,754 A * | 2/1928 | Wood | ............................... | 604/32 |
| 2,148,541 A * | 2/1939 | Dierker | ............................ | 604/40 |
| 3,081,770 A * | 3/1963 | Hunter | ............................ | 600/431 |
| 3,902,495 A * | 9/1975 | Weiss et al. | ..................... | 604/22 |
| 4,240,433 A * | 12/1980 | Bordow | ......................... | 604/540 |
| 4,654,027 A * | 3/1987 | Dragan et al. | .............. | 604/99.03 |
| 4,674,500 A * | 6/1987 | DeSatnick | ..................... | 606/170 |
| 4,762,125 A * | 8/1988 | Leiman et al. | ........... | 128/207.15 |
| 5,070,884 A * | 12/1991 | Columbus et al. | ............ | 600/573 |
| 5,104,384 A * | 4/1992 | Parry | ............................. | 604/192 |
| 5,181,524 A * | 1/1993 | Wanderer et al. | ............. | 600/577 |
| 5,250,065 A * | 10/1993 | Clement et al. | ............... | 606/172 |
| 5,338,292 A * | 8/1994 | Clement et al. | ............... | 604/22 |
| 5,338,311 A * | 8/1994 | Mahurkar | ...................... | 604/195 |
| 5,354,291 A * | 10/1994 | Bales et al. | ...................... | 604/35 |
| 5,403,288 A * | 4/1995 | Stanners | ....................... | 604/232 |
| 5,417,654 A * | 5/1995 | Kelman | ........................... | 604/22 |
| 5,498,244 A * | 3/1996 | Eck | .................................. | 604/198 |
| 5,562,612 A * | 10/1996 | Fox | ................................... | 604/27 |
| 5,571,128 A * | 11/1996 | Shapiro | ........................... | 606/167 |
| 5,591,138 A * | 1/1997 | Vaillancourt | .................. | 604/263 |
| 5,643,304 A * | 7/1997 | Schechter et al. | ............ | 606/171 |
| 5,685,841 A * | 11/1997 | Mackool | .......................... | 604/22 |
| 5,879,338 A * | 3/1999 | Mahurkar | ...................... | 604/195 |
| 5,957,928 A * | 9/1999 | Kirwan, Jr. | ..................... | 606/107 |
| 5,993,409 A * | 11/1999 | Maaskamp | ...................... | 604/22 |
| 6,206,848 B1 * | 3/2001 | Sussman et al. | ................ | 604/27 |
| 6,302,868 B1 * | 10/2001 | Mohammad | .................. | 604/192 |
| 6,589,201 B1 * | 7/2003 | Sussman et al. | ............... | 604/27 |
| 6,921,385 B2 * | 7/2005 | Clements et al. | ............. | 604/141 |
| 7,481,797 B2 * | 1/2009 | Mahurkar | ....................... | 604/195 |
| 8,029,458 B2 * | 10/2011 | Cherif-Cheikh et al. | ...... | 604/47 |
| 8,808,318 B2 * | 8/2014 | Auld et al. | ..................... | 606/166 |

(Continued)

FOREIGN PATENT DOCUMENTS

FR 2720001 A1 * 11/1995 ............. A61M 5/32
WO WO 2010121289 A1 * 10/2010

*Primary Examiner* — Scott Medway
(74) *Attorney, Agent, or Firm* — Kilpatrick Townsend & Stockton LLP

(57) ABSTRACT

The present disclosure relates generally to surgical aspiration and irrigation devices, including methods regarding the same.

17 Claims, 4 Drawing Sheets

(56) References Cited

U.S. PATENT DOCUMENTS

| | | | |
|---|---|---|---|
| 8,911,401 B2* | 12/2014 | Roberts et al. | 604/110 |
| 2003/0093035 A1* | 5/2003 | Mohammed | 604/195 |
| 2004/0176730 A1* | 9/2004 | Wang | 604/263 |
| 2005/0015055 A1* | 1/2005 | Yang | 604/199 |
| 2007/0073219 A1* | 3/2007 | Yang | 604/110 |
| 2010/0010472 A1* | 1/2010 | Moore | 604/520 |
| 2014/0088512 A1* | 3/2014 | Quinn | 604/198 |

* cited by examiner

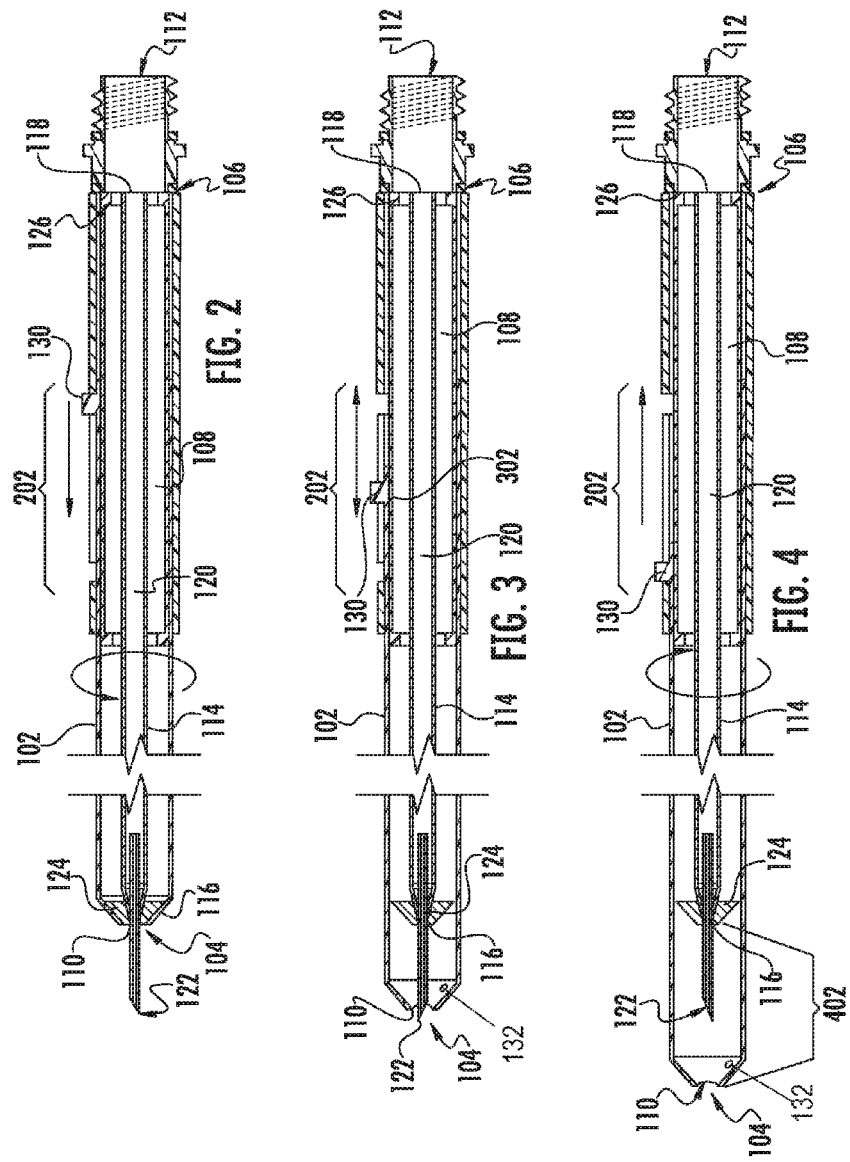

SURGICAL ASPIRATION AND IRRIGATION

CROSS REFERENCE TO RELATED APPLICATION

This application claims priority to and the benefit of U.S. Provisional Application No. 61/752,225, filed Jan. 14, 2013, entitled "SURGICAL ASPIRATION AND IRRIGATION," the full disclosure of which is incorporated herein by reference.

FIELD OF THE INVENTION

The present disclosure relates generally to surgical aspiration and irrigation devices, including methods regarding the same.

BACKGROUND

During medical procedures, doctors and other medical professionals routinely irrigate and/or aspirate the area of the subject around which or within which the medical procedure focuses. When aspirating target areas during these medical procedures, medical professionals often use a needle and syringe to aspirate the target area within the subject or patient. Needles pose a risk of injury to the subject and medical staff and can be difficult to manipulate laproscopically.

Furthermore, during certain medical procedures, it is necessary for a medical professional to irrigate and aspirate a target area simultaneously or at least to have the capability of alternating between irrigation and aspiration fairly quickly.

SUMMARY

The present disclosure relates generally to surgical aspiration and irrigation devices and methods regarding aspiration and irrigation by a single device.

Provided in the present disclosure is a surgical aspiration and irrigation device. The surgical aspiration and irrigation device includes an outer cylinder with a distal end and a proximal end. The outer cylinder forms an outer lumen, and the distal end of outer lumen includes a distal opening. The proximal end of the outer cylinder includes a connector. The connector connects directly or indirectly to a tube, syringe, and/or suction and irrigation handpiece or pump(s).

The surgical aspiration and irrigation device further includes an inner cylinder, and the inner cylinder is located within the outer lumen. The inner cylinder includes a distal end and a proximal end, and the inner cylinder forms an inner lumen. The distal end of the inner cylinder includes a needle and a stopper. The stopper is configured to close the distal opening of the outer lumen around the needle.

Also provided in the surgical aspiration and irrigation device is a valve positioned at the proximal end of the inner lumen. The valve is moveably positioned near the proximal end of the outer lumen. The valve selectively controls the aspiration and irrigation through the inner lumen and the outer lumen. Further, a seal is positioned about an outer circumference of the valve between the valve and the outer cylinder.

Also provided is a method for aspirating or irrigating a surgical target in a subject. The method includes insertion of a surgical aspiration and irrigation device, as fully described herein, into the subject. Irrigation or aspiration is then activated from the tube, syringe, and/or suction and irrigation handpiece or pump(s) connected to the surgical and irrigation device. The surgical aspiration and irrigation device is optionally inserted through a trocar in the subject. The surgical target may include an organ, a cyst, a tumor, an abscess, a pleural cavity, a pericardium cavity, or a blood vessel. The organ is optionally a gall bladder. Optionally, the cyst is an ovarian cyst.

These and other features and advantages of the implementations of the present disclosure will become more readily apparent to those skilled in the art upon consideration of the following detailed description and accompanying drawings, which describe both the preferred and alternative implementations of the present disclosure.

BRIEF DESCRIPTION OF THE DRAWINGS

In the drawings, like reference numbers and designations in the various drawings indicate like elements.

FIG. 2 shows a cross-section of an example surgical aspiration and irrigation device with the distal end of the outer cylinder of the device in an advanced position;

FIG. 3 shows a cross-section of an example surgical aspiration and irrigation device with the distal end of the outer cylinder positioned in an intermediate position between the retracted position and the advanced position;

FIG. 4 shows a cross-section of an example surgical aspiration and irrigation device with the distal end of the outer cylinder of the device in a retracted position;

DETAILED DESCRIPTION

Implementations of the present disclosure now will be described more fully hereinafter. These implementations can be embodied in many different forms and should not be construed as limited to the implementations set forth herein; rather, these implementations are provided by way of example. As used in the specification, and in the appended claims, the singular forms "a," "an," and "the" include plural referents unless the context clearly indicates otherwise. The term "comprising" and variations thereof as used herein is used synonymously with the term "including" and variations thereof and are open, non-limiting terms.

Figure 1:
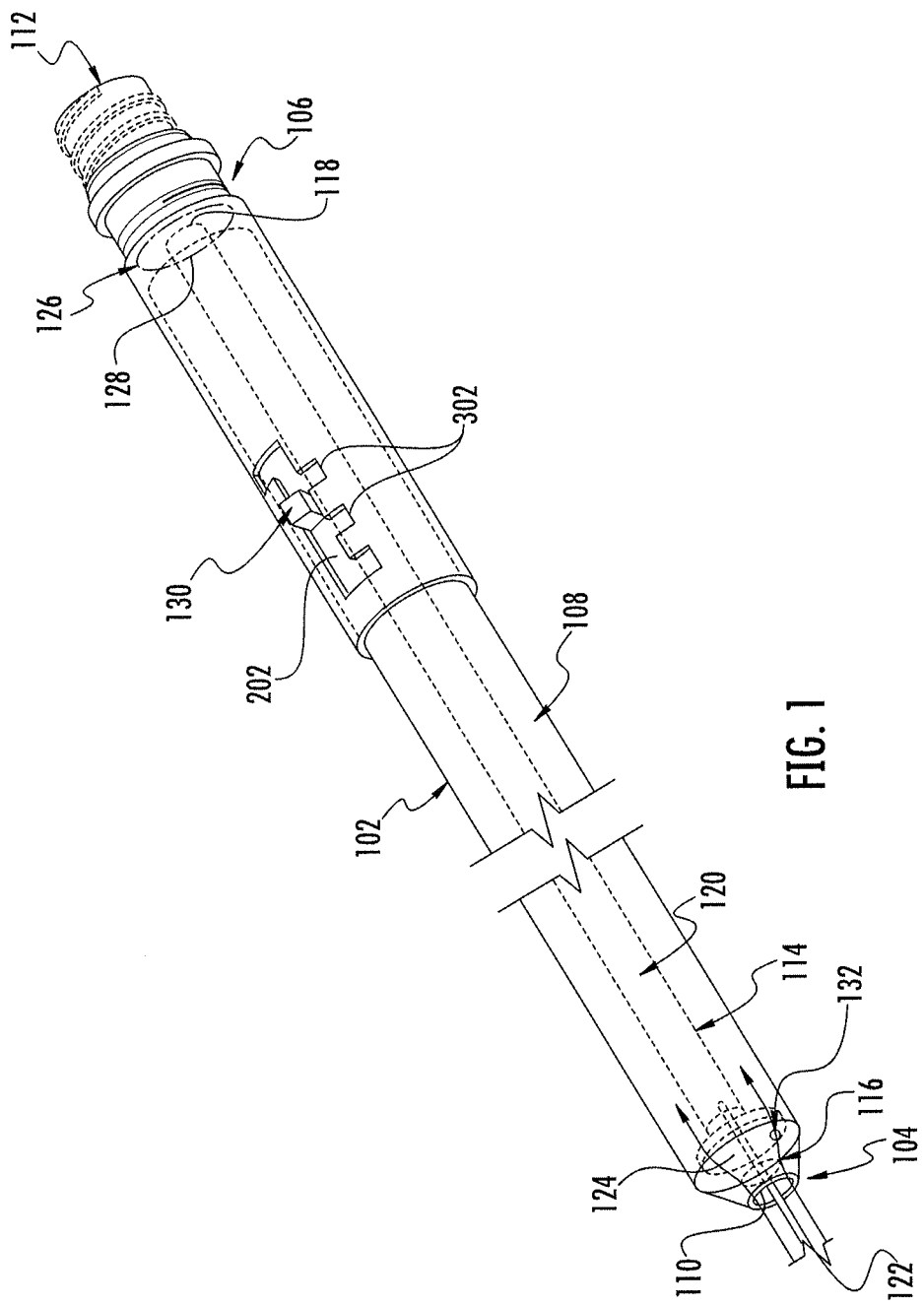
FIG. 1 is a schematic illustration showing an example surgical aspiration and irrigation device.

The present disclosure relates generally to surgical aspiration and irrigation devices, including methods of using the same. The present disclosure includes a surgical aspiration and irrigation device. Referring to FIG. 1, an example surgical aspiration and irrigation device is shown. The example surgical aspiration and irrigation device includes an outer cylinder 102 with a distal end 104 and a proximal end 106. As illustrated in FIGS. 2-4, the distal end 104 is slidingly coupled to the proximal end 106 so that the distal end 104 telescopes outward from the proximal end 106 between retracted and advanced positions, as described in more detail below. The outer cylinder 102 is optionally designed to be inserted through a trocar during a medical procedure. Thus, the size of the outer cylinder 102 is optionally chosen based on the size of the trocar and/or location and accessibility of the surgical target. The outer cylinder 102 forms an outer lumen 108, and the distal end 104 of outer lumen 108 includes a distal opening 110. The proximal end 106 of the outer cylinder 102 includes a connector 112. The connector 112 connects directly or indirectly to a tube, syringe, and/or suction and irrigation handpiece or pump(s). The tube, syringe, or suction and irrigation handpiece optionally connects to one or more pumps (and/or vacuum unit) for providing aspiration and/or irrigation to the surgical aspiration and irrigation device. As used herein, pump is meant to include a unit that either aspirates from a surgical site or a unit that pumps fluid to a surgical site. Optionally a single pumping unit can perform both functions (suction and irrigation).

The surgical aspiration and irrigation device further includes an inner cylinder 114, and the inner cylinder 114 is located within the outer lumen 108. The inner cylinder 114 includes a distal end 116 and a proximal end 118, and the inner cylinder 114 forms an inner lumen 120. The distal end 116 of the inner cylinder 114 includes a needle 122 and a stopper 124. The stopper 124 is configured to close the distal opening 110 of the outer lumen 108 around the needle 122 when the distal opening 110 of the outer lumen 108 approaches the distal end 116 of the inner cylinder 114. Optionally, the needle 122 may include an angled or beveled tip. Furthermore, the distal end 104 of the outer cylinder 102 may include at least one air hole 132. The at least one air hole 132 optionally may prevent tissue or other debris from being aspirated and thereby becoming lodged or otherwise stuck in the inner cylinder 114 and/or outer cylinder 102.

Also provided in the surgical aspiration and irrigation device is a valve 126 positioned at the proximal end 118 of the inner lumen 120. The valve 126 is moveably positioned near the proximal end 106 of the outer lumen 108. The valve 126 selectively controls the aspiration and irrigation through the inner lumen 120 and the outer lumen 108. Further, a seal 128 is positioned about an outer circumference of the valve 126 between the valve 126 and the outer cylinder 102.

The example surgical and aspiration device may also include an advancing element 130 on the exterior portion of the distal end 104 of the outer cylinder 102. Optionally, the advancing element 130 may be connected to the distal end 104 of the outer cylinder 102 in a configuration to advance the distal end 104 of the outer cylinder 102 so that the outer lumen 108 slides over at least a portion of the inner cylinder 114. Thus, the advancing element 130 is designed to move the distal end 104 of the outer cylinder 102 so that the outer lumen 108 slides over at least a portion of the inner cylinder 114. For example, the advancing element 130 may move the distal opening 110 of the outer lumen 108 toward the distal end 116 of the inner cylinder 114. The needle 122 on the distal end 116 of the inner cylinder 114 may optionally be configured to extend through the distal opening 110 of the outer lumen 108 as the distal opening 110 advances toward the distal end 116.

The stopper 124 on the distal end 116 of the inner cylinder 114 may be configured such that the stopper 124 geometrically mates with the distal end 104 of the outer lumen 108. For example, once the stopper 124 geometrically mates with the distal end 104 of the outer lumen 108, the outer lumen 108 stops sliding over the inner cylinder 114 and closes the distal opening 110 of the outer lumen 108 around the needle 122.

Referring now to FIGS. 2-4, an example surgical and aspiration device is shown with the distal end 104 of the outer cylinder 102 in three different positions. Referring to FIG. 2, an example surgical and aspiration device is shown in cross section, revealing the distal end 104 of the outer cylinder 102 in an advanced position. As shown, the distal end 104 of the outer cylinder 102 is optionally in an advanced position when the stopper 124 on the distal end 116 of the inner cylinder 114 geometrically mates with the distal end 104 of the outer lumen 108. The advanced position is achieved by rotating the distal end 104 of the outer cylinder 102 relative to the proximal end 106 of the outer cylinder 102, or vice versa, so as to move the advancing element 130 distally. In the advanced position, the stopper 124 closes the distal opening 110 of the outer lumen 108 around the needle 122. This position limits or eliminates aspiration or irrigation through the outer lumen 108 and allows aspiration or irrigation from the tip of the needle 122.

Referring to FIG. 4, an example surgical and aspiration device is shown in cross section, with the distal end 104 of the outer cylinder 102 in a retracted position. For example, the distal end 104 of the outer cylinder 102 is optionally in a retracted position when the advancing element 130 moves the distal opening 110 of the outer lumen 108 to a maximum distance from the distal end 116 of the inner cylinder 114. The retracted position is achieved by rotating the distal end 104 of the outer cylinder 102 relative to the proximal end 106 of the outer cylinder 102, or vice versa, to move the advancing element 130 proximally. In this position, irrigation or aspiration can occur through the outer chamber but is not necessarily limited thereto.

As shown in FIG. 1, the exterior portion of the proximal end 106 of the outer cylinder 102 may include a path 202 along which the advancing element 130 travels. The path 202 optionally includes one or more intermediate locking slots 302. Referring to FIG. 3, an example surgical and aspiration device showing the distal end 104 of the outer cylinder 102 in a position between the retracted position and the advanced position is shown. For example, the distal end 104 of the outer cylinder 102 may be positioned between the retracted position and the advanced position when the advancing element 130 is positioned in the one or more intermediate locking slots 302.

Figure 5A:
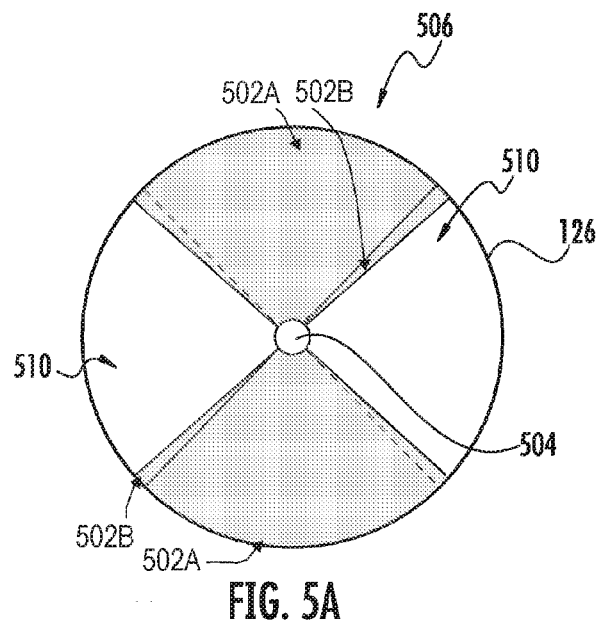
FIGS. 5A and 5B are schematic illustrations showing an example valve in an open and closed position.
Figure 5B:
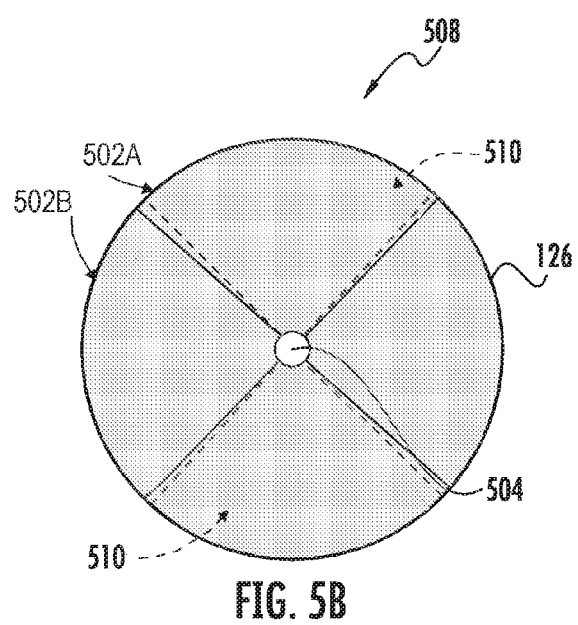

Referring to FIGS. 5A and 5B, an example valve is shown. An example valve 126 may include a first layer 502A and a second layer 502B. Each layer 502A, 502B optionally includes at least two approximately equally-shaped openings 510 to the outer lumen 108. The valve 126 may also include a cannula 504 through the approximate center of the two layers 502A, 502B. The cannula 504 is optionally open to the inner lumen 120. The valve 126 may alternate between an open position 506, as shown in FIG. 5A, and a closed position 508, as shown in FIG. 5B, at the proximal end 106 of the outer lumen 108.

As shown in FIG. 5A, the open position 506 optionally includes overlap between the two approximately equally-shaped openings 510 of the first layer 502A with the two approximately equally-shaped openings 510 of the second layer 502B. For example, the valve 126 is optionally in the open position 506 when the inner cylinder 114 is in the retracted position, thereby allowing irrigation or aspiration from the tube, syringe, or suction and irrigation handpiece therethrough the outer lumen 108. Referring now to FIG. 5B, the closed position 508 optionally includes non-overlap between the two approximately equally-shaped openings 510 of the first layer 502A with the two approximately equally-shaped openings 510 of the second layer 502B. For example, the valve 126 is optionally in the closed position 508 when the inner cylinder 114 is in the advanced position, thereby allowing irrigation or aspiration from the tube, syringe, or suction and irrigation handpiece therethrough the inner lumen 120 and preventing irrigation or aspiration therethrough the outer lumen 108.

In an example surgical aspiration and irrigation device, the inner lumen 120 and the outer lumen 108 may be configured to aspirate or irrigate therethrough the distal ends of the inner lumen 120 and outer lumen 108. For example, when the inner cylinder 114 is in the advanced position, the inner lumen 120 is optionally configured to aspirate or irrigate and the outer lumen 108 is optionally not configured to aspirate or irrigate.

Figure 6:
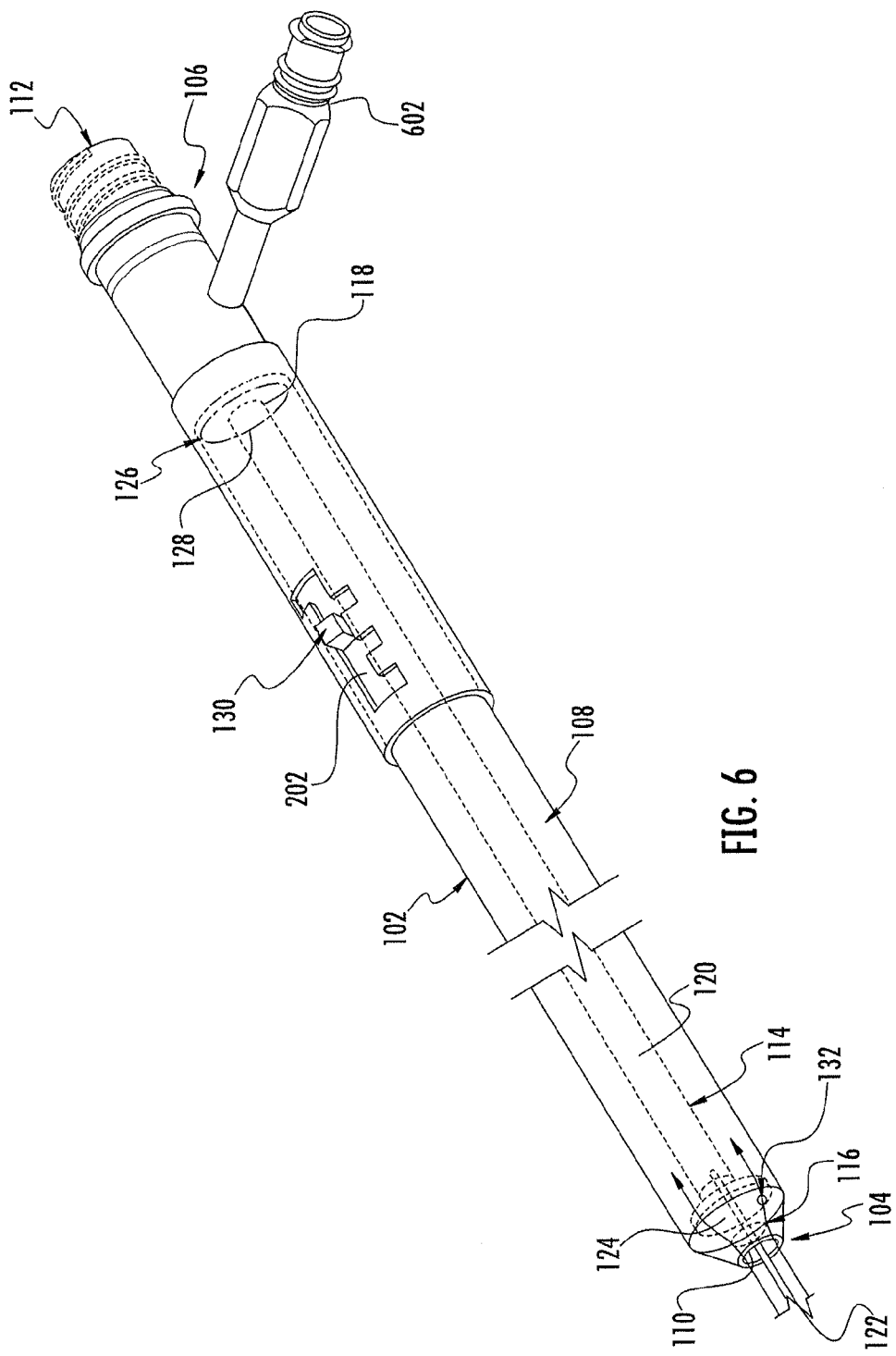
FIG. 6 is a schematic illustration showing an example surgical aspiration and irrigation device.

Referring now to FIG. 6, an example surgical and irrigation device is shown. The inner cylinder 114 of an example surgical and irrigation device may include an inner connector 602. For example, the inner connector 602 may optionally be connected directly or indirectly to a tube, syringe, or suction and irrigation handpiece or pump(s).

Suction and irrigation pumps are known to one of skill in the art. Separate units, one for suction and one for irrigation, are optionally used with the described suction and irrigation device.

Also provided in the present disclosure is a method for aspirating or irrigating a surgical target in a subject. The method includes the insertion of a surgical and aspiration device, as described fully herein, into a subject, optionally during laparoscopic surgery, and then activating irrigation or aspiration from the tube, syringe, or suction and irrigation handpiece or pump(s) connected to the device. The method may be accomplished by insertion of the surgical and aspiration device through a trocar in the subject. For example, the surgical target may include an organ, a cyst, a tumor, an abscess, a pleural cavity, a pericardium cavity, a peritoneum cavity, a vein, a blood vessel, or an artery. For example, the organ optionally may include a gall bladder. The cyst optionally includes an ovarian cyst.

As used throughout, but subject is meant an individual. Preferably, the subject is a mammal such as a primate, and, more preferably, a human. Non-human primates are subjects as well. The term subject includes domesticated animals, such as cats, dogs, etc., livestock (for example, cattle, horses, pigs, sheep, goats, etc.) and laboratory animals (for example, ferret, chinchilla, mouse, rabbit, rat, gerbil, guinea pig, etc.). Thus, veterinary uses and medical uses are contemplated herein.

One of skill in the art would select a suction/irrigation device as shown herein having a selected diameter and length. Should a selection is based on the procedure to be performed, the size and age of the subject, and other factors.

It is understood that the disclosure is not to be limited to the specific embodiments disclosed and that modifications and other embodiments are intended to be included within the scope of the appended claims.

That which is claimed is:

1. A surgical aspiration and irrigation device, comprising:
   an outer cylinder having a distal end and a proximal end and forming an outer lumen, wherein the distal end of the outer lumen comprises a distal opening, and wherein the proximal end of the outer cylinder comprises a connector for connecting directly or indirectly to a tube, syringe, or suction and irrigation handpiece;
   an inner cylinder located within the outer lumen wherein the inner cylinder has a distal end and a proximal end and forms an inner lumen, wherein the distal end of the inner cylinder comprises a needle and a stopper configured to close the distal opening of the outer lumen around the needle;
   an advancing element connected to an exterior portion of the distal end of the outer cylinder, wherein the advancing element is positionable in one or more intermediate locking slots on an exterior portion of the proximal end of the outer cylinder and is configured to move the distal end of the outer cylinder between:
      an advanced position, wherein the distal end of the outer lumen geometrically mates with the stopper on the distal end of the inner cylinder such that the stopper closes the distal opening of the outer lumen around the needle, and
      a retracted position, wherein the distal opening of the outer lumen is moved a maximum distance from the distal end of the inner cylinder; and
   a valve positioned at the proximal end of the inner lumen and moveably positioned near the proximal end of the outer lumen, wherein the valve is configured to control selectively aspiration and irrigation therethrough the inner lumen and the outer lumen, and wherein a seal is positioned about an outer circumference of the valve between the valve and outer cylinder, wherein the valve comprises
      a first layer and a second layer, wherein each layer comprises at least two approximately equally-shaped openings to the outer lumen, and
      a cannula through an approximate center of the two layers, wherein the cannula is open to the inner lumen.

2. The surgical aspiration and irrigation device of claim 1, wherein the valve is configured to alternate between an open position and a closed position at the proximal end of the outer lumen.

3. The surgical aspiration and irrigation device of claim 2, wherein the open position comprises overlap between the at least two approximately equally-shaped openings of the first layer with the at least two approximately equally-shaped openings of the second layer.

4. The surgical aspiration and irrigation device of claim 2, wherein the closed position comprises non-overlap between the at least two approximately equally-shaped openings of the first layer with the at least two approximately equally-shaped openings of the second layer.

5. The surgical aspiration and irrigation device of claim 3, wherein the valve is in the open position when the inner cylinder is in the retracted position, thereby allowing irrigation or aspiration from the tube, syringe, or suction and irrigation handpiece therethrough the outer lumen.

6. The surgical aspiration and irrigation device of claim 4, wherein the valve is in the closed position when the inner cylinder is in the advanced position, thereby allowing irrigation or aspiration from the tube, syringe, or suction and irrigation handpiece therethrough the inner lumen and preventing irrigation or aspiration therethrough the outer lumen.

7. The surgical aspiration and irrigation device of claim 1, wherein the inner lumen and the outer lumen are configured to aspirate or irrigate therethrough the distal ends of the inner lumen and the outer lumen.

8. The surgical aspiration and irrigation device of claim 7, wherein, when the inner cylinder is in the advanced position, the inner lumen is configured to aspirate or irrigate and the outer lumen is not configured to aspirate or irrigate.

9. The surgical aspiration and irrigation device of claim 1, wherein the needle comprises an angled tip needle or a bevel tip needle.

10. The surgical aspiration and irrigation device of claim 1, further comprising at least one air hole in the distal end of the outer cylinder, wherein the at least one air hole prevents tissue or other debris from being aspirated and thereby becoming lodged or otherwise stuck in the inner cylinder and/or the outer cylinder.

11. The surgical aspiration and irrigation device of claim 1, wherein the outer cylinder is designed to be inserted therethrough a trocar.

12. The surgical aspiration and irrigation device of claim 1, wherein the inner cylinder further comprises an inner connector for connecting to a tube or a syringe.

13. A method of aspirating or irrigating a surgical target in a subject comprising inserting the device of claim 1 into the subject and activating irrigation or aspiration from the tube, syringe, or suction and irrigation handpiece connected to the device.

14. The method of claim 13, wherein the surgical target comprises a human organ, a cyst, a tumor, an abscess, a pleural cavity, a pericardium cavity, a peritoneum cavity, a vein, a blood vessel, or an artery.

15. The method of claim 14, wherein the organ is a gall bladder.

16. The method of claim 14, wherein the cyst is an ovarian cyst.

17. The method of claim 13, wherein the device of claim 1 is inserted through a trocar in the subject.

\* \* \* \* \*